United States Patent
Suehara et al.

(10) Patent No.: US 10,039,902 B2
(45) Date of Patent: Aug. 7, 2018

(54) ACTUATING MEMBER AND MEDICAL DEVICE

(71) Applicant: Terumo Kabushiki Kaisha, Tokyo (JP)

(72) Inventors: Satoru Suehara, Kanagawa (JP); Ryousuke Yamazaki, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 698 days.

(21) Appl. No.: 14/571,889

(22) Filed: Dec. 16, 2014

(65) Prior Publication Data
US 2015/0100020 A1    Apr. 9, 2015

Related U.S. Application Data

(63) Continuation of application No. PCT/JP2012/075057, filed on Sep. 28, 2012.

(51) Int. Cl.
*A61M 25/01*    (2006.01)

(52) U.S. Cl.
CPC .... *A61M 25/0147* (2013.01); *A61M 25/0136* (2013.01); *A61M 25/0138* (2013.01); *A61M 25/0144* (2013.01)

(58) Field of Classification Search
CPC .......... A61M 25/0133; A61M 25/0136; A61M 25/0144; A61M 25/0147
See application file for complete search history.

(56) References Cited

U.S. PATENT DOCUMENTS

| | | | |
|---|---|---|---|
| 4,483,326 A | * | 11/1984 | Yamaka ............... A61B 1/0057 600/141 |
| 5,441,483 A | | 8/1995 | Avitall |
| 2006/0142695 A1 | | 6/2006 | Knudson |
| 2008/0139886 A1 | | 6/2008 | Tatsuyama |

FOREIGN PATENT DOCUMENTS

| | | |
|---|---|---|
| JP | 2002-512534 A | 4/2002 |
| JP | 2006-187614 A | 7/2006 |
| JP | 2008-142199 A | 6/2008 |

OTHER PUBLICATIONS

International Search Report dated Oct. 30, 2012 issued in Application No. PCT/JP2012/075057.

* cited by examiner

*Primary Examiner* — Laura Bouchelle
(74) *Attorney, Agent, or Firm* — Foley & Lardner LLP

(57) ABSTRACT

An actuating member includes: a first movement member and a second movement member which are located at a proximal side of the elongated member and are configured to be relatively movable toward and away from each other along an axial direction of the elongated member; a push-pull member that includes a first connection portion configured to be connected to the first movement member, a first extension portion extending from the first connection portion toward a distal side in the axial direction of the elongated member, a second connection portion configured to be connected to the second movement member, and a second extension portion extending from the second connection portion toward the distal side in the axial direction of the elongated member; and an operation member configured to operate the movement of the first movement member and the second movement member.

20 Claims, 11 Drawing Sheets

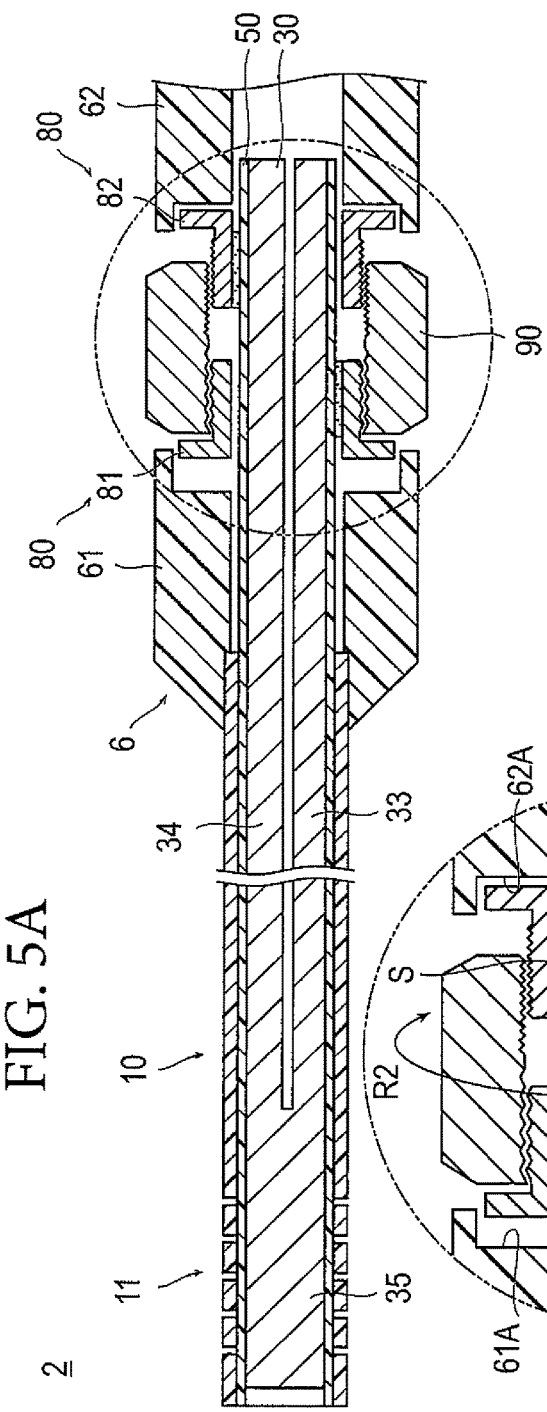
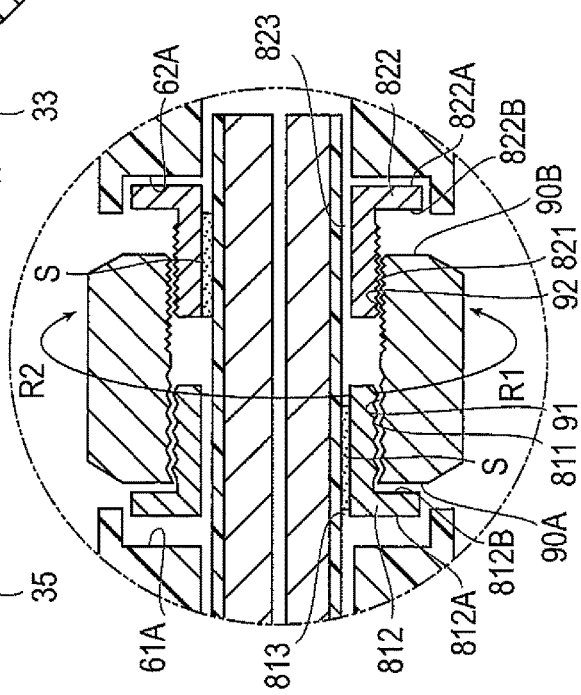
FIG. 5A
FIG. 5B the # ACTUATING MEMBER AND MEDICAL DEVICE

CROSS-REFERENCE TO RELATED PATENT APPLICATIONS

This application is a continuation application filed under 35 U.S.C. 111(a) claiming the benefit under 35 U.S.C. §§ 120 and 365(c) of PCT International Application No. PCT/JP2012/075057, filed Sep. 28, 2012 the disclosures of which is hereby incorporated by reference in its entirety.

BACKGROUND

Technical Field

The present disclosure relates to an actuating member that causes an elongated member for medical use to perform a predetermined operation and a medical device that includes the actuating member.

Background Art

In a medical field, an elongated flexible member has been used as a medical device for accessing a living body, for example, to provide medication into the living body, allow for suction or injection of various fluids, and allow for introduction of a medical apparatus into the living body. Prior to the introduction of the medical apparatus, this elongated member is inserted into a lumen of the living body (blood vessel or body cavity) and is guided to a target site such as a treatment site or a peripheral site thereof. In usage described above, in order to properly guide the elongated member to the target site, it is necessary to introduce the elongated member along a bending path such as the lumen of the living body. Therefore, in some cases, the elongated member may be used integrally with a actuating member capable of performing a bending operation when actuated by a user's manual operation.

JP-A-2008-142199 discloses an actuating member including a push-pull member to be connected to the elongated member, a pulley around which the push-pull member is wound and a handle which causes the pulley to be rotatably operated, and an endoscope in which the actuating member is incorporated. The actuating member rotates the above-described handle arranged on a proximal side of the endoscope around an axis orthogonal to an axial direction of the elongated member, thereby winding the push-pull member and performing the bending operation.

The above-described actuating member in the related art adopts a configuration where the actuating member is bendable by arranging the push-pull member to be wound around the pulley and changing an operation direction for pushing and pulling the push-pull member from a linear direction to a circumferential direction. Therefore, a relatively low rigid wire is used in the push-pull member. For this reason, there is a possibility that push-pull force cannot be satisfactorily transmitted to the elongated member via the wire.

In addition, the pulley around which the push-pull member is wound is arranged on an axial line of the elongated member so as to move the push-pull member in an axial direction. However, for example, when disposing a lumen which is continuous from a distal side to a proximal side of the elongated member, the pulley may interfere with the lumen. Accordingly, the pulley has to be arranged to be offset in a direction orthogonal to the axial direction. Therefore, an actuating mechanism becomes large, thereby causing a problem in that the entire apparatus becomes large as a result.

SUMMARY OF THE INVENTION

An objective of certain embodiments of the present invention is to provide an actuating member which can efficiently transmit forward and backward movements of a push-pull member to an elongated member and enable the entire apparatus to be of minimal size.

According to one embodiment, there is provided an actuating member that causes an elongated flexible member for medical use to perform a predetermined operation. The actuating member includes: a first movement member and a second movement member which are arranged on a proximal side of the elongated member and are disposed to be relatively movable toward and away from each other along an axial direction of the elongated member; a push-pull member that includes a first connection portion to be connected to the first movement member, a first extension portion extending from the first connection portion to a distal side in the axial direction of the elongated member, a second connection portion to be connected to the second movement member, and a second extension portion extended from the second connection portion to the distal side in the axial direction of the elongated member, and that moves in the axial direction of the elongated member so as to be pushed and pulled by a movement of the first movement member and the second movement member; and an operation member that operates the movement of the first movement member and the second movement member. The push-pull member transmits the movement of the first movement member and the second movement member to the elongated member, thereby causing the elongated member to perform at least one of a forward and backward operation and a bending operation.

Thus, without the operation direction being changed, the push-pull member is pushed and pulled in the axial direction of the elongated member, thereby causing the elongated member to perform the forward and backward operation or the bending operation. Therefore, it is possible to efficiently transmit the forward and backward movement of the push-pull member to the elongated member. In addition, the push-pull member and the operation member can be arranged on a straight line in the axial direction of the elongated member, and do not need to be arranged by being offset in the direction orthogonal to the axial direction of the elongated member. Therefore, it is possible to minimize the size of the entire medical device.

In one aspect, the operation member is configured to be capable of respectively moving the first movement member and the second movement member in opposite directions along the axial direction, and the bending operation of the elongated member is performed by moving the first movement member and the second movement member.

Thus, the bending operation of the elongated member is performed by moving the first movement member and the second movement member in the opposite direction to each other. Therefore, it is possible to bend the elongated member by using a smaller movement amount of the first movement member and the second movement member, thereby improving operability of the actuating member.

In one aspect, the operation member is configured to have a tubular member where a first operation screw portion which can mesh with a first screw portion disposed in the first movement member and a second operation screw portion which can mesh with a second screw portion disposed in the second movement member and threaded in a direction opposite to the first screw portion are formed on an inner peripheral surface thereof, and is disposed so as to be capable of operating the movement of the first movement member and the second movement member by rotating the operation member.

Thus, the first operation screw portion disposed on the inner peripheral surface of the operation member and the first screw portion disposed in the first movement member, and the second operation screw portion disposed on the inner peripheral surface of the operation member and the second screw portion disposed in the second movement member and threaded in a direction opposite to the first screw portion can respectively mesh with each other. Therefore, it is possible to bend the elongated member by rotatably operating the operation member, thereby improving the operability of the actuating member.

In one aspect, as the operation member is rotated so that a meshing amount of the first operation screw portion with the first screw portion and a meshing amount of the second operation screw portion with the second screw portion are increased, the operation member causes the elongated member to be bent by moving the first movement member and the second movement member relatively toward each other.

In one aspect, the elongated member is bent by the increase in the meshing amount between the first operation screw portion disposed on the inner peripheral surface of the operation member and the first screw portion disposed in the first movement member, and between the second operation screw portion disposed on the inner peripheral surface of the operation member and the second screw portion disposed in the second movement member and threaded in a direction opposite to the first screw portion. Therefore, the meshing amount between the screw portions is increased in a state where the elongated member is bent, thereby enabling the elongated member to reliably hold the bent state.

In one aspect, the operation member is configured to be capable of moving the first movement member and the second movement member in the same direction along the axial direction so as to have respectively different movement amounts, and the forward and backward operation and the bending operation of the elongated member are performed by moving the first movement member and the second movement member.

Thus, the forward and backward operation and the bending operation of the elongated member are performed. Therefore, it is possible to provide the actuating member having higher performance.

In one aspect, the operation member is configured to have a tubular member where a first operation screw portion which can mesh with a first screw portion disposed in the first movement member and a second operation screw portion which can mesh with a second screw portion disposed in the second movement member and including a screw pitch different from that of the first screw portion are formed on an inner peripheral surface thereof, and is disposed so as to be capable of operating the movement of the first movement member and the second movement member by rotating the operation member.

Thus, the first operation screw portion disposed on the inner peripheral surface of the operation member and the first screw portion disposed in the first movement member, and the second operation screw portion disposed on the inner peripheral surface of the operation member and the second screw portion disposed in the second movement member and including a screw pitch different from that of the first screw portion can respectively mesh with each other. Therefore, it is possible to cause the elongated member to move forward and backward and to be bent by rotatably operating the operation member, thereby improving the operability of the actuating member.

In one aspect, as the operation member is rotated so that a meshing amount of a screw portion formed to have a small screw pitch, out of the first screw portion and the second screw portion, with the first operation screw portion or the second operation screw portion is increased, the operation member causes the elongated member to be bent by relatively moving the first movement member and the second movement member away from each other.

Thus, the elongated member is bent by the increase in the meshing amount of the screw portion formed to have the small screw pitch. Therefore, the meshing amount between the screw portions is increased in a state where the elongated member is bent, thereby enabling the elongated member to reliably hold the bent state.

In one aspect, as the operation member is rotated so that a meshing amount of a screw portion formed to have a large screw pitch, out of the first screw portion and the second screw portion, with the first operation screw portion or the second operation screw portion is increased, the operation member causes the elongated member to be bent by moving the first movement member and the second movement member relatively away from each other.

Thus, it is possible to suppress bias in the meshing amount between two screw portions located in both ends. Therefore, balance in the load applied to the push-pull member becomes more equal during the bending, thereby improving the operability.

In one aspect, the actuating member further includes a visual checking portion that enables a movement amount of the first movement member and the second movement member to be visually checked.

Thus, it is possible to check the movement amount of the first movement member and the second movement member by using the visual checking portion, thereby improving the operability of the actuating member.

In one embodiment a medical device comprises an actuating member and an elongated flexible member that is caused to perform at least one operation of a forward and backward operation and a bending operation by the actuating member.

Thus, it is possible to efficiently transmit the forward and backward movement of the push-pull member to the elongated member, and it is possible to provide the medical device including the actuating member which can minimize the size of the entire apparatus.

BRIEF DESCRIPTION OF THE DRAWINGS

FIG. 5A is a side cross-sectional view illustrating a medical device according to a second embodiment.

FIG. 5B is a magnified side cross-sectional view of a portion of FIG. 5A

DETAILED DESCRIPTION

First Embodiment

Hereinafter, an embodiment of the present invention will be described with reference to the drawings. The drawings may be exaggeratedly illustrated for convenience of description and thus, dimensional proportions thereof may be different from actual proportions. In addition, in the following description, a manually operating side of a medical device 1 according to a first embodiment of the present invention is referred to as a "proximal side", and a side to be inserted into a lumen of a living body is referred to as a "distal side".

A configuration of the medical device 1 according to the first embodiment of the present invention will be described.

Figure 1:
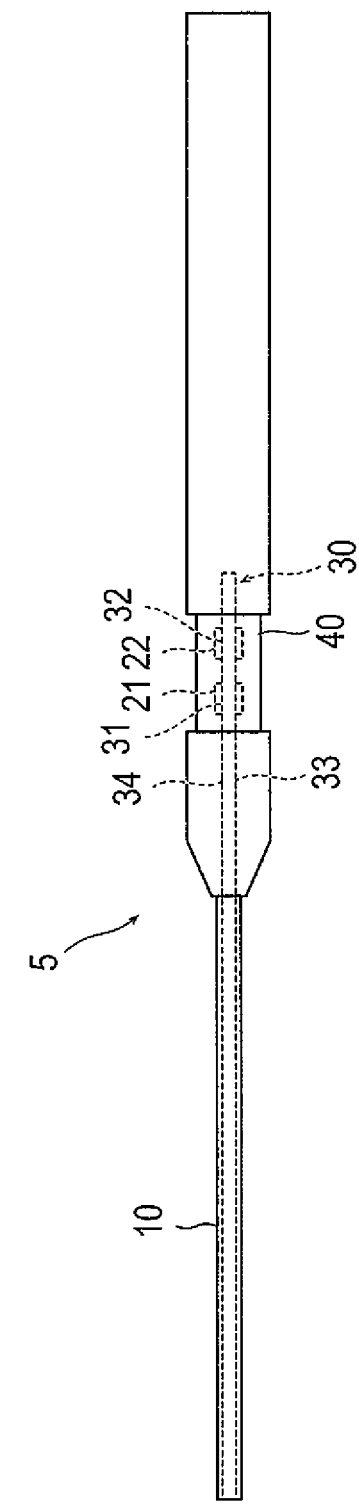
FIG. 1 is a schematic configuration diagram illustrating a medical device according to a first embodiment of the present invention.
Figure 2A:
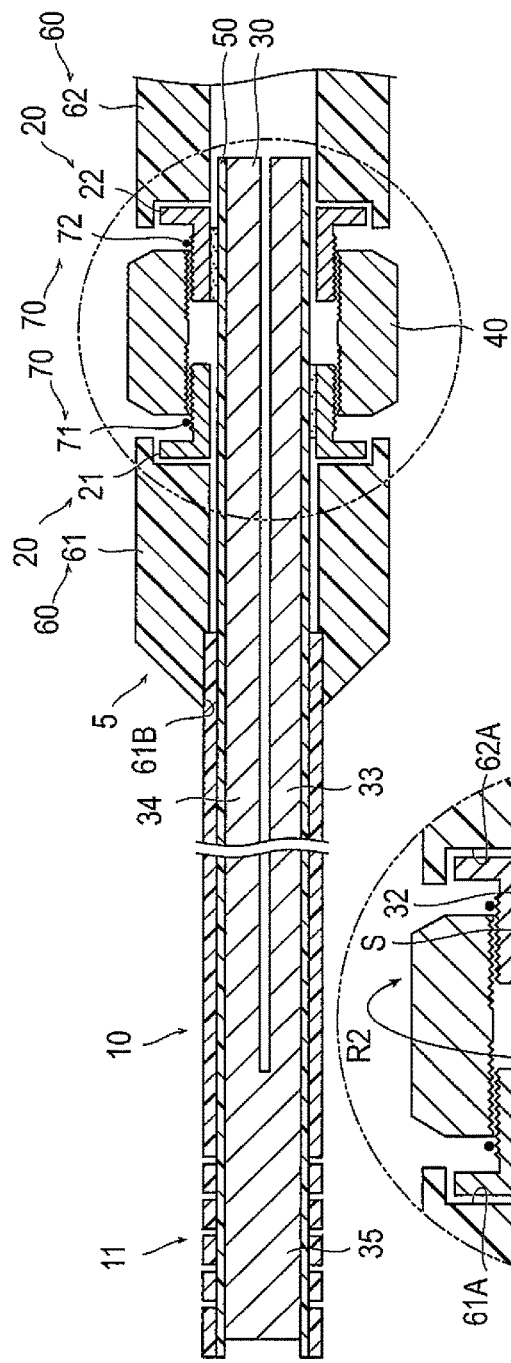
FIG. 2A is a side cross-sectional view illustrating the medical device according to the first embodiment.

FIG. 1 is a schematic configuration diagram illustrating the medical device 1 according to the first embodiment of the present invention. FIG. 2A is a side cross-sectional view illustrating the medical device 1 according to the first embodiment.

In short, as illustrated in FIG. 1, the medical device 1 according to the first embodiment of the present invention includes a flexible elongated member 10 for medical use and an actuating member 5 which causes the elongated member 10 to perform a predetermined operation. The actuating member 5 includes a first movement member 21 and a second movement member 22 which are arranged in the proximal side of the elongated member 10 and which are disposed to be movable relatively toward and away from each other along an axial direction of the elongated member 10; and a push-pull member 30 that includes a first connection portion 31 to be connected to the first movement member 21, a first extension portion 33 extended from the first connection portion 31 to the distal side in the axial direction of the elongated member 10, a second connection portion 32 to be connected to the second movement member 22, and a second extension portion 34 extended from the second connection portion 32 to the distal side in the axial direction of the elongated member 10, and that moves in the axial direction of the elongated member 10 so as to be pushed and pulled by a movement of the first movement member 21 and the second movement member 22. In addition, the actuating member 5 further includes an operation member 40 that operates the movement of the first movement member 21 and the second movement member 22. The push-pull member 30 can cause the elongated member 10 to perform a bending operation by transmitting the movement of the first movement member 21 and the second movement member 22 to the elongated member 10. Herein, the configuration will be described in detail.

Figure 2B:
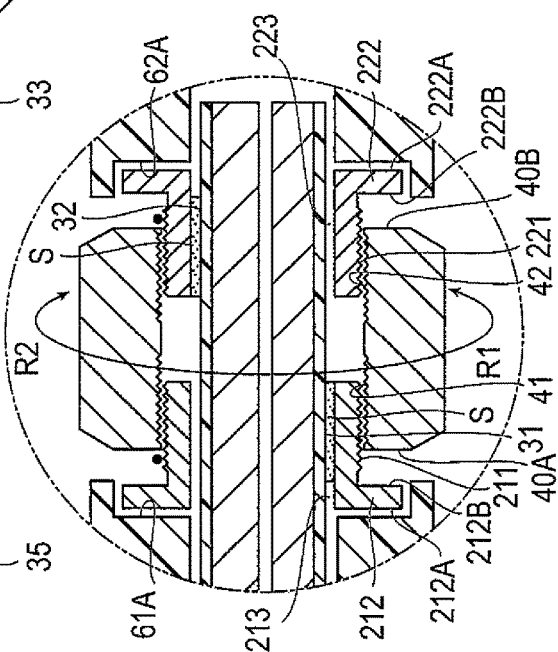
FIG. 2B is a magnified side cross-sectional view of a portion of FIG. 2A

As illustrated in FIGS. 2A and 2B, the actuating member 5 includes a movement member 20 which is arranged on the proximal side of the elongated member 10 and which is disposed to be movable along the axial direction of the elongated member 10; the push-pull member 30 which is connected to the movement member 20 and moves in the axial direction of the elongated member 10 by being pushed and pulled by a movement of the movement member 20; the operation member 40 which operates the movement of the movement member 20; a sealing portion 50 which is disposed on an outer periphery of the push-pull member 30 and seals a fluid flowing in the push-pull member 30; a base portion 60 which is disposed on an outer periphery of the proximal side of the sealing portion and supports the movement member 20 and the push-pull member 30; and a visual checking portion 70 which allows a movement amount of the movement member 20 to be visually checked.

The movement member 20 pushes and pulls the push-pull member 30 to cause the elongated member 10 to perform the bending operation. The movement member 20 has the first movement member 21 and the second movement member 22 which are disposed to be movable relatively toward and away from each other along the axial direction of the elongated member 10.

The first movement member 21 is connected to the first connection portion 31 via the sealing portion 50 by an adhesive S, and pushes and pulls the first extension portion 33 in the axial direction of the elongated member 10. In addition, the first movement member 21 is arranged closer to the distal side than the second movement member 22. In addition, the first movement member 21 has a first screw portion 211 disposed in the proximal side, a first protruding portion 212 which is disposed in the distal side and protrudes in a radial direction, and a first through-hole 213 which is disposed in the axial direction of the elongated member 10.

The first screw portion 211 is threaded so that the first movement member 21 is moved to the distal side when the operation member 40 is rotated in a direction of R1, and the first movement member 21 is moved to the proximal side when the operation member 40 is rotated in a direction of R2. A screw pitch of the first screw portion 211 is preferably 1 mm to 5 mm, and more preferably 2 mm to 3 mm. In addition, it is preferable that a thread ridge of the first screw portion 211 have a trapezoidal shape. According to this shape, a contact area between the first screw portion 211 and a first operation screw portion 41 (to be described later) is increased. Therefore, it is possible to reliably hold a bent state of the elongated member 10.

When the operation member 40 is rotated in the direction of R1, the first protruding portion 212 is moved to the distal side. When the first protruding portion 212 is moved by a predetermined amount, a distal surface 212A of the first protruding portion 212 comes into contact with a recess 61A of a support portion 61 (to be described later). Therefore, it is possible to restrict the movement amount of the first movement member 21 to the distal side. In addition, the first protruding portion 212 is moved to the proximal side when the operation member 40 is rotated in the direction of R2. When the first protruding portion 212 is moved by a predetermined amount, a proximal surface 212B of the first protruding portion 212 comes into contact with a distal surface 40A of the operation member 40. Therefore, it is possible to restrict the movement amount of the first movement member 21 to the proximal side.

The push-pull member 30 and the sealing portion 50 are inserted into the first through-hole 213.

The second movement member 22 is connected to the second connection portion 32 via the sealing portion 50 by the adhesive S, and pushes and pulls the second extension portion 34 in the axial direction of the elongated member 10. In addition, the second movement member 22 has a second screw portion 221 disposed in the distal side, a second protruding portion 222 which is disposed in the proximal side and protrudes in the radial direction, and a second through-hole 223 which is disposed in the axial direction of the elongated member 10.

The second screw portion 221 is threaded so that the second movement member 22 is moved to the proximal side when the operation member 40 is rotated in the direction of R1, and the second movement member 22 is moved to the distal side when the operation member 40 is rotated in the direction of R2. That is, the second screw portion 221 and the first screw portion 211 are threaded in an opposite direction to each other. The screw pitch of the second screw portion 221 is preferably 1 mm to 5 mm, and more preferably 2 mm to 3 mm. In addition, it is preferable that the thread ridge of the second screw portion 221 have the trapezoidal shape similar to that of the thread ridge of the first screw portion 211.

When the operation member 40 is rotated in the direction of R1, the second protruding portion 222 is moved to the proximal side. When the second protruding portion 222 is moved by a predetermined amount, a proximal surface 222A of the second protruding portion 222 comes into contact with a recess 62A of a gripping portion 62 (to be described later). Therefore, it is possible to restrict the movement amount of the second movement member 22 to the proximal side. In addition, when the operation member 40 is rotated in the direction of R2, the second protruding portion 222 is moved to the distal side. When the second protruding portion 222 is moved by a predetermined amount, a distal surface 222B of the second protruding portion 222 comes into contact with a proximal surface 40B of the operation member 40. Therefore, it is possible to restrict the movement amount of the second movement member 22 to the distal side.

The push-pull member 30 and the sealing portion 50 are inserted into the second through-hole 223.

Figure 3:
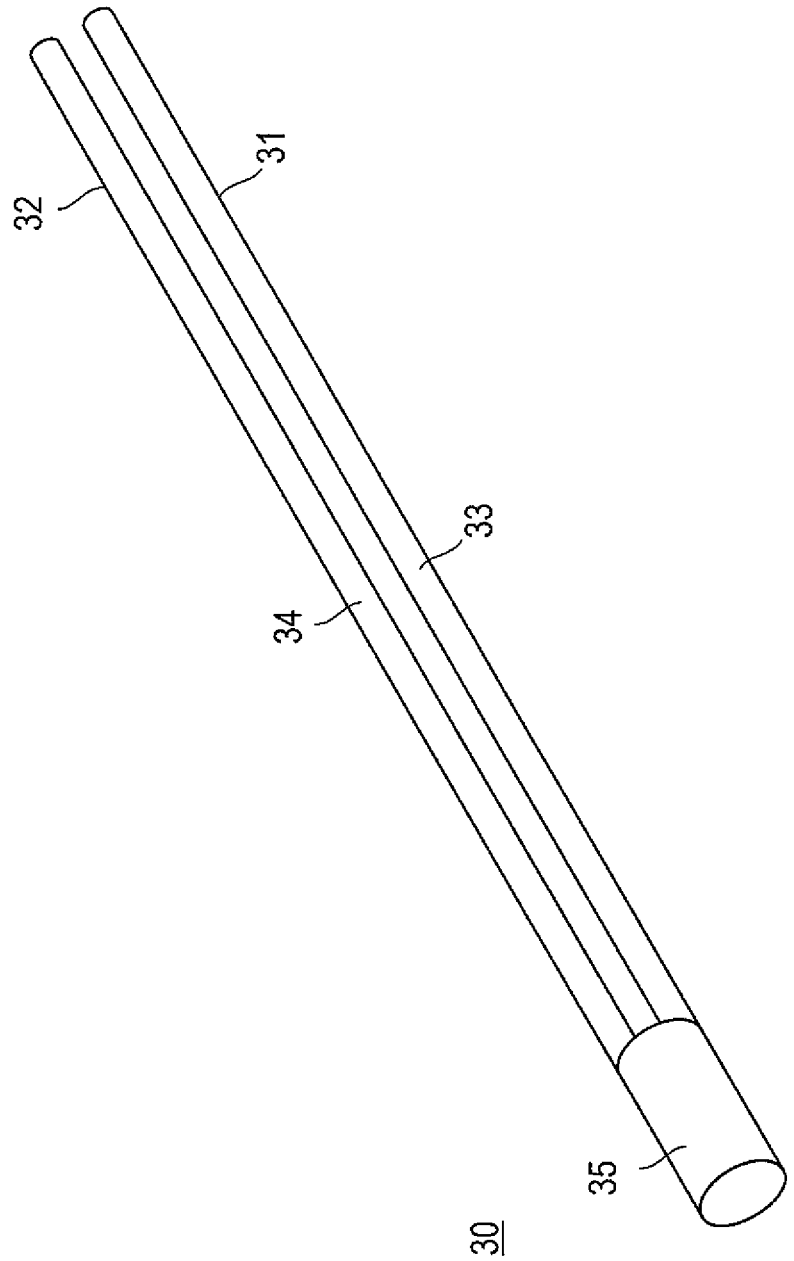
FIG. 3 is a perspective view illustrating a push-pull member.

FIG. 3 is a perspective view illustrating the push-pull member 30.

The push-pull member 30 is pushed and pulled in the axial direction of the elongated member 10 by the movement of the first movement member 21 and the second movement member 22, thereby causing the elongated member 10 to perform the bending operation. As illustrated in FIG. 3, the push-pull member 30 has the first connection portion 31 to be connected to the first movement member 21, the first extension portion 33 extended from the first connection portion 31 to the distal side in the axial direction of the elongated member 10, the second connection portion 32 to be connected to the second movement member 22, the second extension portion 34 extended from the second connection portion 32 to the distal side in the axial direction of the elongated member 10, and a bending portion 35 which is connected to the distal side of the first extension portion 33 and the second extension portion 34, and which is to be bent by relatively pushing and pulling the first extension portion 33 and the second extension portion 34. In the present embodiment, the first connection portion 31 and the second connection portion 32 are respectively connected to the first movement member 21 and the second movement member 22 via the sealing portion 50. However, without disposing the sealing portion 50, the first connection portion 31 and the second connection portion 32 may also be respectively connected to the first movement member 21 and the second movement member 22. In addition, the sealing portion 50 may be arranged inside the push-pull member 30. In addition, the push-pull member 30 may be configured so as to be capable of pushing and pulling the distal side of the elongated member 10, and for example, the push-pull member 30 may be a traction wire, a plate-shaped belt member or the like.

The first connection portion 31 connects the first movement member 21 and the first extension portion 33 via the adhesive S and the sealing portion 50.

The second connection portion 32 connects the second movement member 22 and the second extension portion 34 via the adhesive S and the sealing portion 50.

The first extension portion 33 transmits the movement of the first movement member 21 to the bending portion 35.

The second extension portion 34 transmits the movement of the second movement member 22 to the bending portion 35.

The bending portion 35 is bent by the movement of the first movement member 21 and the second movement member 22, and bends the distal side of the elongated member 10.

The push-pull member 30 has the above-described configuration. Accordingly, when the first extension portion 33 is arranged closer to the distal side than the second extension portion 34 by the above-described movement, the bending portion 35 is bent upward. In contrast, when the first extension portion 33 is arranged closer to the proximal side than the second extension portion 34, the bending portion 35 is bent downward.

The operation member 40 is configured to be capable of respectively moving the first movement member 21 and the second movement member 22 in the opposite direction to each other along the axial direction, and the bending operation of the elongated member 10 is performed by moving the first movement member 21 and the second movement member 22. In addition, the operation member 40 is configured to have a tubular member where the first operation screw portion 41 which can mesh with the first screw portion 211 disposed in the first movement member 21 and the second operation screw portion 42 which can mesh with the second screw portion 221 disposed in the second movement member 22 and threaded in the direction opposite to the first screw portion 211 are formed on an inner peripheral surface thereof, and is disposed so as to be capable of operating the movement of the first movement member 21 and the second movement member 22 by rotating the operation member 40. In addition, as the operation member 40 is rotated (in the direction of R2) so that a meshing amount of the first operation screw portion 41 and the first screw portion 211, and a meshing amount of the second operation screw portion 42 and the second screw portion 221 are increased, the operation member 40 causes the elongated member 10 to be bent by moving the first movement member 21 and the second movement member 22 relatively toward each other. In addition, an outer periphery of the operation member 40 is configured to have a hexagonal shape, and thus has a shape which enables an operator to rotate the operation member 40 with his or her fingers.

The sealing portion 50 seals a fluid flowing in the push-pull member 30. The sealing portion 50 is fixed in close contact with the outer periphery of the push-pull member 30. The fixing method is not particularly limited, and for example, the sealing portion 50 can be fixed by an adhesive, brazing, fusion bonding or the like. For example, a material for configuring the sealing portion 50 is a material which has excellent biocompatibility, that is, a fluorine resin such as ethylene tetrafluoroethylene (ETFE) copolymer and polytetrafluoroethylene (PTFE), and polyolefin such as polyethylene (PE) and polypropylene (PP), a thermoplastic resin such as polyamide, polyester, polyurethane or the like.

The base portion 60 supports the elongated member 10, the movement member 20 and the push-pull member 30. The base portion 60 has the support portion 61 which is arranged in the distal side of the first movement member 21 and supports the first movement member 21 and the push-pull member 30, and the gripping portion 62 which is arranged in the proximal side of the second movement member 22, supports the second movement member 22 and the push-pull member 30, and is gripped by an operator for manual therapy. The base portion 60 includes, for example, a hard resin material.

The support portion 61 supports the elongated member 10, the first movement member 21 and the push-pull member 30. The support portion 61 has the recess 61A which restricts the movement of the first movement member 21 to the distal side by coming into contact with the distal surface 212A of the first protruding portion 212, and the recess 61B which is disposed in the distal side and into which the elongated member 10 is inserted.

The gripping portion 62 supports the second movement member 22 and the push-pull member 30, and is gripped by the operator for manual therapy. The gripping portion 62 has the recess 62A which is disposed in the distal side and restricts the movement of the second movement member 22 to the proximal side by coming into contact with the proximal surface 222A of the second protruding portion 222.

The visual checking portion 70 enables the operator to visually check the movement amount of the movement member 20. The visual checking portion 70 has a first visual checking portion 71 which is disposed in the first screw portion 211 of the first movement member 21 so as to check the movement amount of the first movement member 21, and a second visual checking portion 72 which is disposed in the second screw portion 222 of the second movement member 22 so as to check the movement amount of the second movement member 22. For example, the visual checking portion 70 is a marker, but may be a scale without being limited thereto.

The elongated member 10 is inserted into the recess 61B, and the bending portion 35 is bent so that the distal side is bent. The elongated member 10 has a weak rigidity portion 11 which can be easily bent in the distal side. For example, the weak rigidity portion 11 is a slit. However, without being limited thereto, a material having rigidity lower than that of other portions may be used. In the present embodiment, the weak rigidity portion 11 is disposed in two locations in a vertical direction, but may be disposed in at least one location. For example, a material for configuring the elongated member 10 is a material which has excellent biocompatibility, that is, a fluorine resin such as ethylene tetrafluoroethylene (ETFE) copolymer and polytetrafluoroethylene (PTFE), and polyolefin such as polyethylene (PE) and polypropylene (PP), a thermoplastic resin such as polyamide, polyester, polyurethane or the like. In addition, a structure having the bending portion in combination with a tubular metal member used in an endoscope or the like may also be used.

Figure 4:
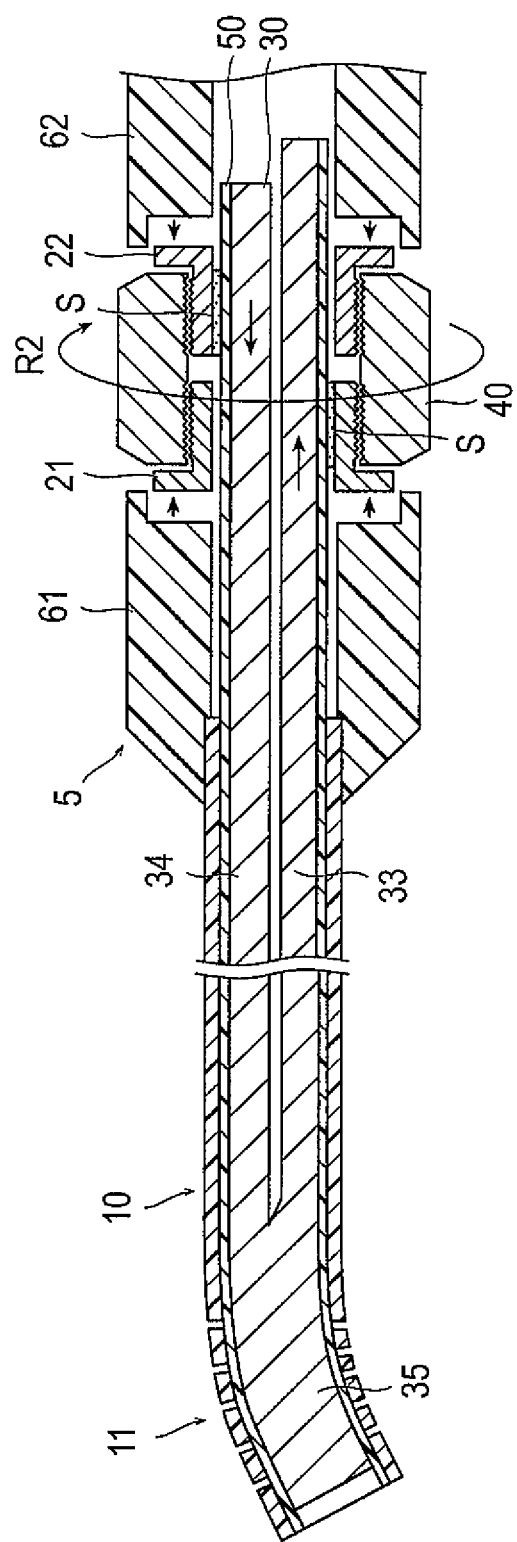
FIG. 4 is a side cross-sectional view illustrating the medical device of FIG. 2A when a distal side of an elongated member is bent downward.

Next, a method of bending the elongated member 10 by using the actuating member 5 according to the first embodiment of the present invention will be described with reference to FIG. 4. FIG. 4 is a side cross-sectional view illustrating the medical device 1 when the distal side of the elongated member 10 is bent downward.

As illustrated in FIG. 4, the operator rotates the operation member 40 in the direction of R2. Then, the first movement member 21 is moved to the proximal side, and the second movement member 22 is moved to the distal side. In this case, the first movement member 21 is connected to the first extension portion 33 by the adhesive S, and the second movement member 22 is connected to the second extension portion 34 by the adhesive S. Accordingly, the first extension portion 33 is moved to the proximal side, and the second extension portion 34 is moved to the distal side. When the first extension portion 33 is moved to the proximal side and the second extension portion 34 is moved to the distal side, the bending portion 35 is bent downward. If the bending portion 35 is bent downward, the distal side of the elongated member 10 is bent downward.

As described above, according to the first embodiment of the present invention, the push-pull member 30 is pushed and pulled in the axial direction of the elongated member 10 without the operation direction thereof being changed, thereby causing the elongated member 10 to perform the forward and backward operation. Accordingly, it is possible to efficiently transmit the forward and backward movement of the push-pull member 30 to the elongated member 10. In addition, the push-pull member 30 and the operation member 40 can be arranged on a straight line in the axial direction of the elongated member 10, and do not need to be arranged by being offset in the direction orthogonal to the axial direction of the elongated member 10. Therefore, it is possible to minimize the size of the entire medical device 1.

In addition, the operation member 40 is configured to be capable of moving the first movement member 21 and the second movement member 22 respectively in the opposite direction to each other along the axial direction. The bending operation of the elongated member 10 is performed by moving the first movement member 21 and the second movement member 22. Therefore, the elongated member 10 can be bent with a smaller movement amount of the first movement member 21 and the second movement member 22, thereby improving the operability of the actuating member 5.

In addition, the operation member 40 is configured to have a tubular member configured such that the first operation screw portion 41 which can mesh with the first screw portion 211 disposed in the first movement member 21 and the second operation screw portion 42 which can mesh with the second screw portion 221 disposed in the second movement member 22 and threaded in the direction opposite to the first screw portion 211 are formed on an inner peripheral surface thereof, and is disposed so as to be capable of operating the movement of the first movement member 21 and the second movement member 22 by rotating the operation member 40. Therefore, it is possible to bend the elongated member 10 by rotating the operation member 40, thereby improving the operability of the actuating member 5.

In addition, as the operation member 40 is rotated so that a meshing amount of the first operation screw portion 41 with the first screw portion 211, and a meshing amount of the second operation screw portion 42 with the second screw portion 221 are increased, the operation member 40 causes the elongated member 10 to be bent by moving the first movement member 21 and the second movement member 22 toward each other. Therefore, the meshing amount between the screw portions is increased in a state where the elongated member 10 is bent, thereby enabling the elongated member 10 to reliably hold the bent state.

The visual checking portion 70, which enables the movement amount of the first movement member 21 and the second movement member 22 to be visually checked, is further provided. Therefore, it is possible to check the movement amount of the first movement member 21 and the second movement member 22 by using the visual checking portion 70, thereby improving the operability of the actuating member 5.

In addition, it is possible to efficiently transmit the forward and backward movement of the push-pull member 30 to the elongated member 10, and it is possible to provide the medical device 1 including the actuating member 5 which can minimize the size of the entire apparatus.

Second Embodiment

Next, a second embodiment of the present invention will be described. Parts common to the first embodiment will not be described, and parts characterized only in the second embodiment will be described.

FIG. 5A is a side cross-sectional view illustrating a medical device 2 according to the second embodiment of the present invention.

As illustrated in FIGS. 5A and 5B, the medical device 2 according to the second embodiment of the present invention has an actuating member 6. The actuating member 6 has a movement member 80 which is arranged in the proximal side of the elongated member 10 and disposed to be movable along the axial direction of the elongated member 10, and an operation member 90 which operates a movement of the movement member 80. Other configurations are the same as those of the first embodiment.

The movement member 80 pushes and pulls the push-pull member 30 to cause the elongated member 10 to perform the forward and backward operation and the bending operation. The movement member 80 has a first movement member 81 and a second movement member 82 which are disposed to be movable relatively toward and away from each other along the axial direction of the elongated member 10.

The first movement member 81 is connected to the first connection portion 31 via the sealing portion 50 by the adhesive S, and pushes and pulls the first extension portion 33 in the axial direction of the elongated member 10. In addition, the first movement member 81 is arranged closer to the distal side than the second movement member 82. In addition, the first movement member 81 has a first screw portion 811 disposed in the proximal side, and a first protruding portion 812 which is disposed in the distal side and protrudes in the radial direction.

The first screw portion 811 is threaded so that the first movement member 81 is moved to the proximal side when the operation member 90 is rotated in the direction of R1, and the first movement member 81 is moved to the distal side when the operation member 90 is rotated in the direction of R2. The screw pitch of the first screw portion 811 is preferably 2 mm to 5 mm, and more preferably 3 mm to 4 mm.

When the operation member 90 is rotated in the direction of R1, the first protruding portion 812 is moved to the proximal side. When the first protruding portion 812 is moved by a predetermined amount, a distal surface 812A of the first protruding portion 812 comes into contact with a recess 61A of the support portion 61. Therefore, it is possible to restrict the movement amount of the first movement member 81 to the distal side. In addition, when the operation member 90 is rotated in the direction of R2, the first protruding portion 812 is moved to the distal side. When the first protruding portion 812 is moved by a predetermined amount, a proximal surface 812B of the first protruding portion 812 comes into contact with a distal surface 90A of the operation member 90. Therefore, it is possible to restrict the movement amount of the first movement member 81 to the proximal side.

The second movement member 82 is connected to the second connection portion 32 via the sealing portion 50 by the adhesive S, and pushes and pulls the second extension portion 34 in the axial direction of the elongated member 10. In addition, the second movement member 82 has a second screw portion 821 disposed in the distal side, and a second protruding portion 822 which is disposed in the proximal side and protrudes in the radial direction.

The second screw portion 821 is threaded so that the second movement member 82 is moved to the proximal side when the operation member 90 is rotated in the direction of R1, and the second movement member 82 is moved to the distal side when the operation member 90 is rotated in the direction of R2. That is, the second screw portion 821 and the first screw portion 811 are threaded in the same direction. In addition, the second screw portion 821 is formed to have a screw pitch which is shorter than that of the first screw portion 811. The screw pitch of the second screw portion 821 is preferably 1 mm to 4 mm, and more preferably 1 mm to 2 mm. In the present embodiment, the second screw portion 821 is formed to have the screw pitch which is shorter than that of the first screw portion 811. However, the second screw portion 821 may be formed to have the screw pitch which is longer than that of the first screw portion 811.

When the operation member 90 is rotated in the direction of R1, the second protruding portion 822 is moved to the proximal side. When the second protruding portion 822 is moved by a predetermined amount, a proximal surface 822A of the second protruding portion 822 comes into contact with the recess 62A of the gripping portion 62. Therefore, it is possible to restrict the movement amount of the second movement member 82 to the proximal side. In addition, when the operation member 90 is rotated in the direction of R2, the second protruding portion 822 is moved to the distal side. When the second protruding portion 822 is moved by a predetermined amount, a distal surface 822B of the second protruding portion 822 comes into contact with a proximal surface 90B of the operation member 90. Therefore, it is possible to restrict the movement amount of the second movement member 82 to the distal side.

The operation member 90 is configured to be capable of moving the first movement member 81 and the second movement member 82 in the same direction along the axial direction so as to have respectively different movement amounts, and the forward and backward operation and the bending operation of the elongated member 10 are performed by moving the first movement member 81 and the second movement member 82. In addition, the operation member 90 is configured to have a tubular member where the first operation screw portion 91 which can mesh with the first screw portion 811 disposed in the first movement member 81 and the second operation screw portion 92 which can mesh with the second screw portion 821 disposed in the second movement member 82 and having the shorter screw pitch than that of the first screw portion 811 are formed on an inner peripheral surface thereof, and is disposed so as to be capable of operating the movement of the first movement member 81 and the second movement member 82 by rotating the operation member 90. In addition, as the operation member 90 is rotated (in the direction of R2) so that a meshing amount of the second screw portion 821 with the second operation screw portion 92 is increased, the operation member 90 causes the elongated member 10 to be bent by moving the first movement member 81 and the second movement member 82 relatively away from each other.

Figure 6:
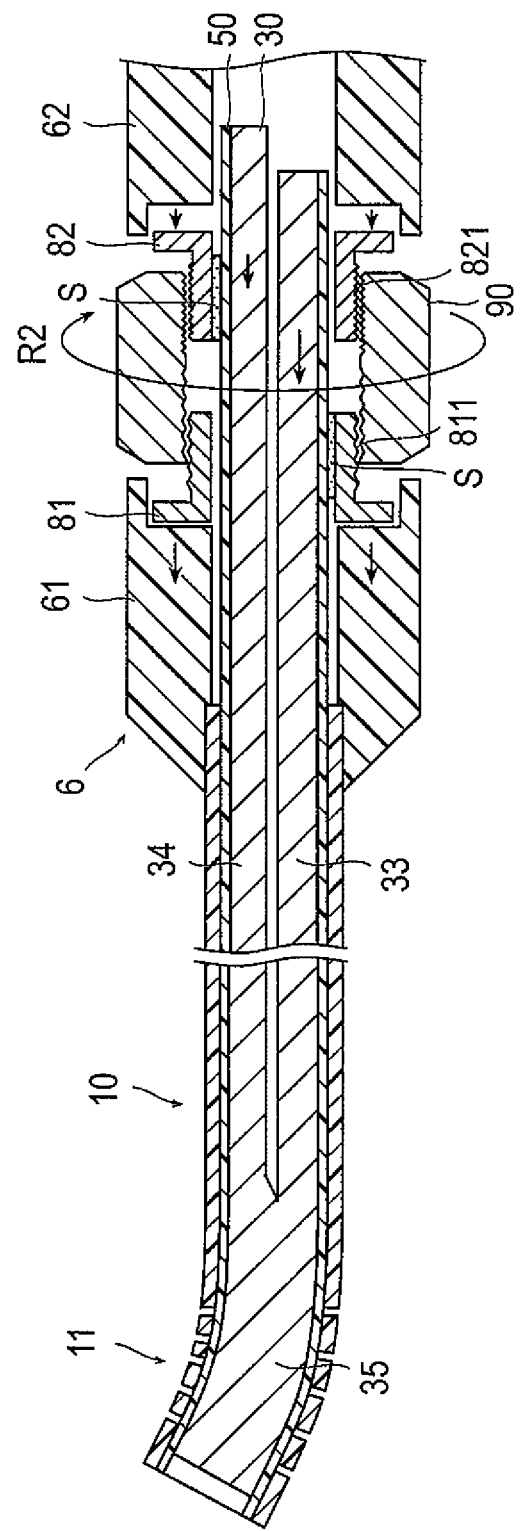
FIG. 6 is a side cross-sectional view illustrating the medical device of FIG. 5A when a distal side of an elongated member is bent upward.

Next, referring to FIG. 6, a method will be described in which the distal side of the elongated member 10 is bent by using the actuating member 6 according to the second embodiment of the present invention. FIG. 6 is a side cross-sectional view illustrating the medial device 2 when the distal side of the elongated member 10 is bent upward.

As illustrated in FIG. 6, an operator rotates the operation member 90 in the direction of R2. Then, the first movement member 81 is moved to the distal side and the second movement member 22 is also moved to the distal side. In this case, the first movement member 81 is connected to the first extension portion 33 by the adhesive S, and the second movement member 82 is connected to the second extension portion 34 by the adhesive S. Accordingly, the first extension portion 33 is moved to the distal side, and the second extension portion 34 is also moved to the distal side. Then, because the second screw portion 821 is formed to have the shorter screw pitch than that of the first screw portion 811, when the operation member 90 is rotated, the first extension portion 33 is moved closer to the distal side than the second extension portion 34. Therefore, the bending portion 35 is moved to the distal side and is bent upward. If the bending portion 35 is moved to the distal side and is bent upward, the elongated member 10 is moved to the distal side, and the distal side of the elongated member 10 is bent upward.

As described above, according to the second embodiment of the present invention, the push-pull member 30 is pushed and pulled in the axial direction of the elongated member 10 without the operation direction thereof being changed, thereby causing the elongated member 10 to perform the forward and backward operation and the bending operation. Accordingly, it is possible to efficiently transmit the forward and backward movement of the push-pull member 30 to the elongated member 10. In addition, the push-pull member 30 and the operation member 90 can be arranged on a straight line in the axial direction of the elongated member 10, and do not need to be arranged by being offset in the direction orthogonal to the axial direction of the elongated member 10. Therefore, it is possible to minimize the size of the entire medical device 2.

In addition, the operation member 90 is configured to be capable of moving the first movement member 81 and the second movement member 82 in the same direction along the axial direction so as to have respectively different movement amounts, and the forward and backward operation and the bending operation of the elongated member 10 are performed by moving the first movement member 81 and the second movement member 82. Therefore, it is possible to provide the actuating member 6 having higher performance.

In addition, the operation member 90 is configured to have a tubular member where the first operation screw portion 91 which can mesh with the first screw portion 811 disposed in the first movement member 81 and the second operation screw portion 92 which can mesh with the second screw portion 821 disposed in the second movement member 82 and having the shorter screw pitch than that of the first screw portion 811 are formed on an inner peripheral surface thereof, and is disposed so as to be capable of operating the movement of the first movement member 81 and the second movement member 82 by rotating the operation member 90.

Therefore, it is possible to cause the elongated member 10 to move forward and backward and to be bent by rotating the operation member 90, thereby improving the operability of the actuating member 6.

In addition, as the operation member 90 is rotated so that a meshing amount of the second screw portion 821 with the second operation screw portion 92 is increased, the operation member 90 causes the elongated member 10 to be bent by moving the first movement member 81 and the second movement member 82 away from each other. Therefore, the meshing amount between the screw portions is increased in a state where the elongated member 10 is bent, thereby enabling the elongated member 10 to reliably hold the bent state.

Hereinafter, modification examples of the above-described embodiments will be described as an example.

First Modification Example

Figure 7:
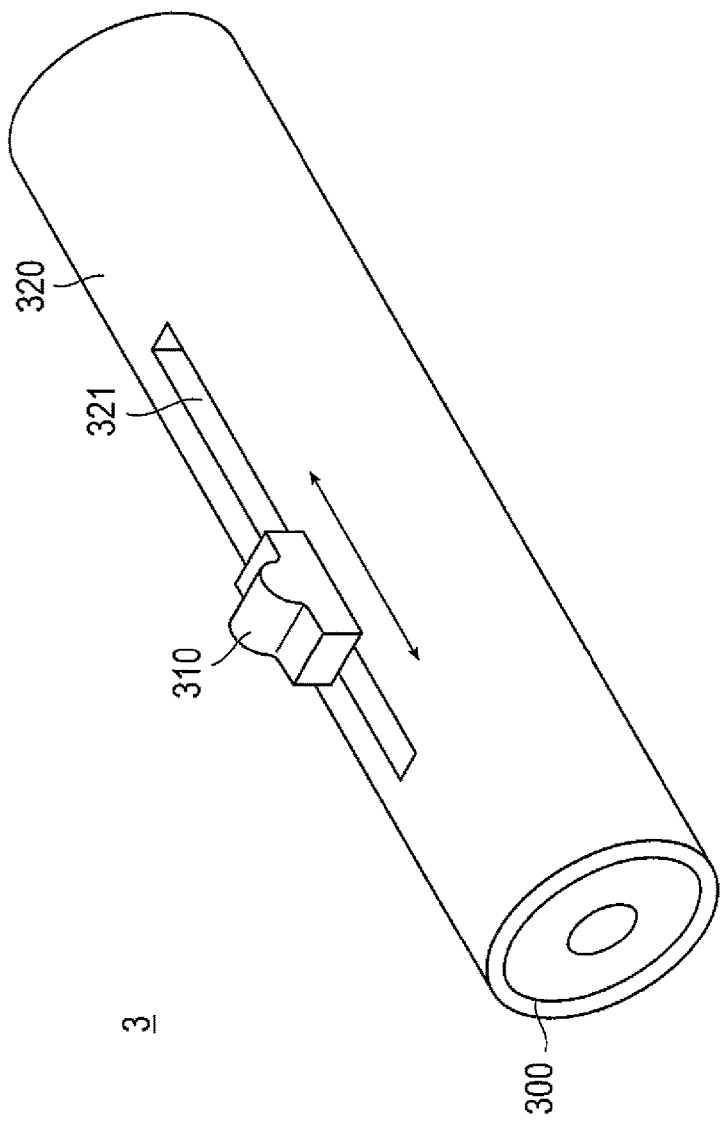
FIG. 7 is a perspective view illustrating a gripping portion, an operation member, and a guide grove of a medical device according to a first modification example.
Figure 8:
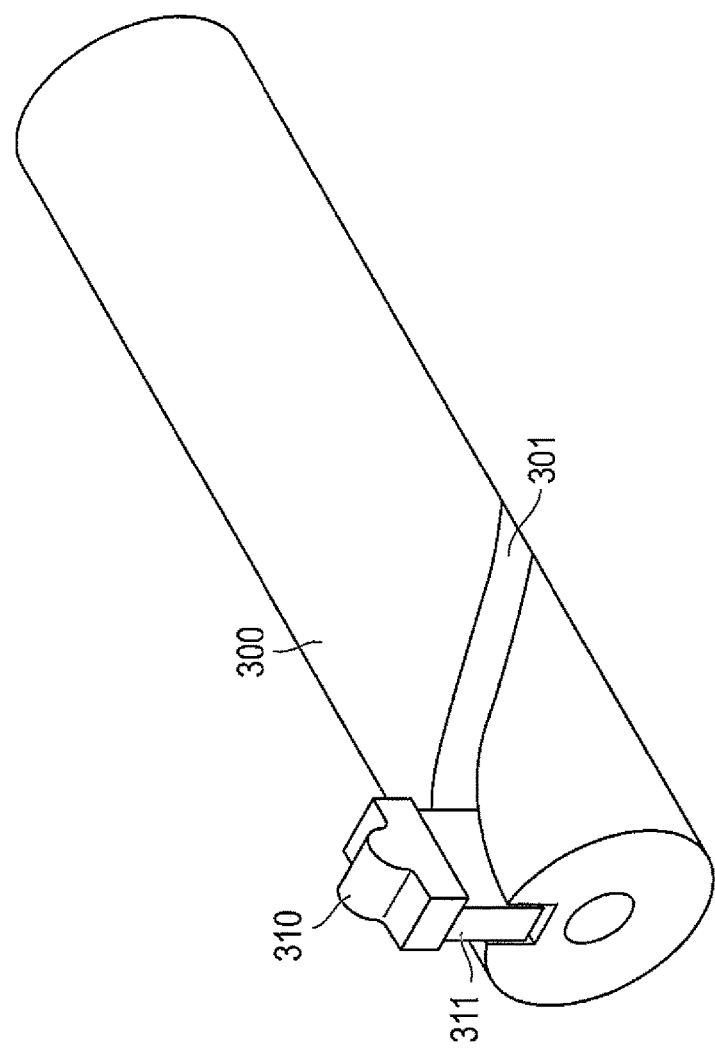
FIG. 8 is a perspective view illustrating a movement member, a spiral groove, and the operation member of the medical device of FIG. 7.
Figure 9:
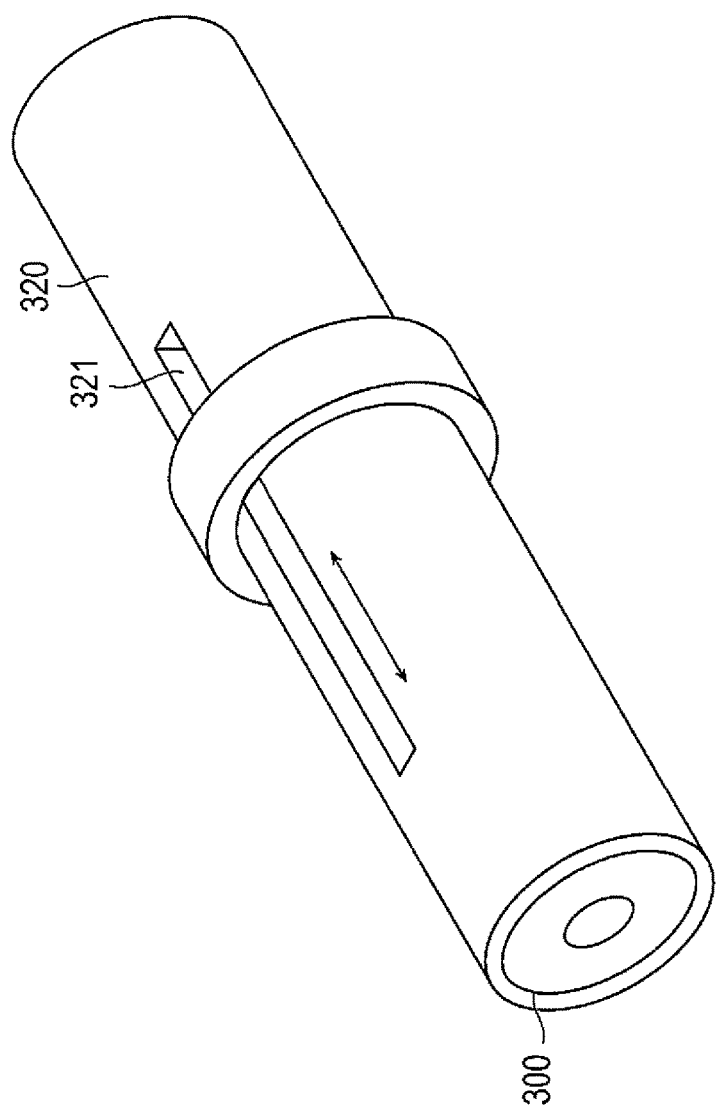
FIG. 9 is a perspective view of when the operation member is a ring type in the first modification example.

FIG. 7 is a perspective view illustrating a medical device 3 according to a first modification example. In addition, FIG. 8 is a perspective view illustrating a movement member 300 and an operation member 310 of the medical device 3. In FIG. 7, the push-pull member 30 and the elongated member 10 are omitted in the illustration. As illustrated in FIGS. 7 and 8, the medical device 3 according to the first modification example includes the movement member 300 having a spiral groove 301 on an outer periphery thereof; the operation member 310 having a convex portion 311 disposed to be fitted to the spiral groove 301 and an operation portion 312 which can be operated by an operator's fingers; and a gripping portion 320, which is disposed on the outer periphery of the movement member 300, has a guide groove 321 disposed so that the operation member 310 is slidable in the axial direction of the elongated member 10, and is gripped by the operator for manual therapy. According to this configuration, if the operator slides the operation portion 312 in the axial direction of the elongated member 10, the convex portion 311 of the operation member 310 moves through the spiral groove 301, thereby enabling the movement member 300 to be pivoted. Accordingly, similar to the above-described first and second embodiments, it is possible to cause the elongated member 10 to perform the bending operation and the forward and backward operation. As illustrated in FIG. 9, the operation member 310 may be a ring type.

Second Modification Example

Figure 10:
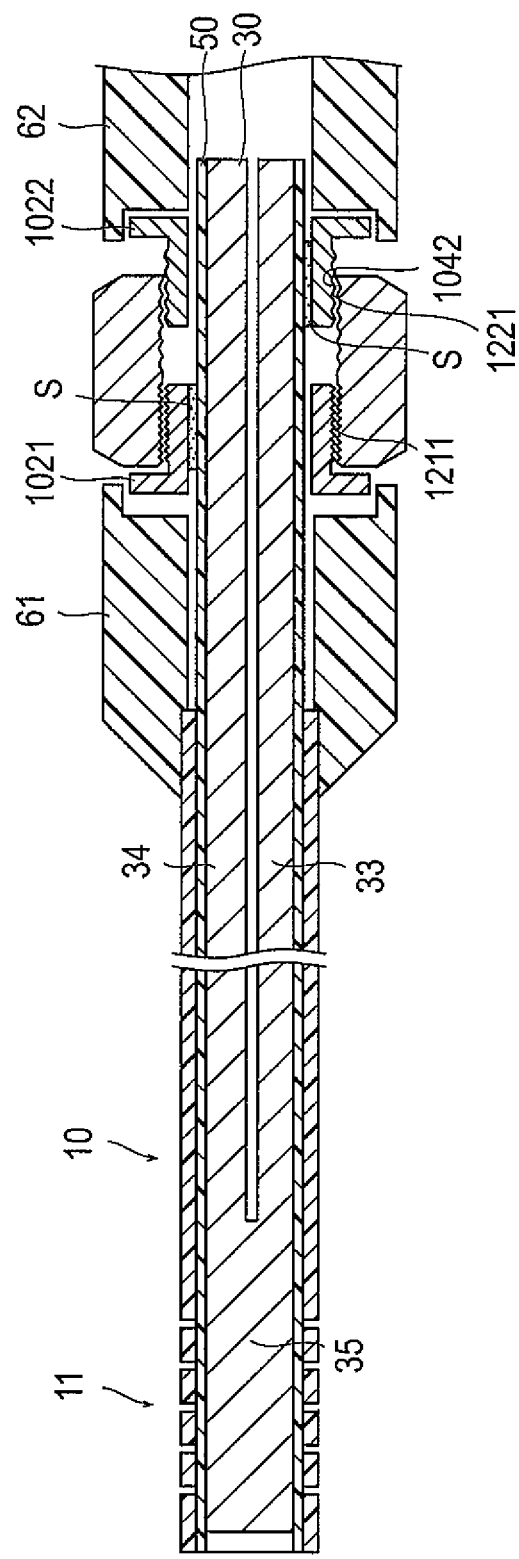
FIG. 10 is a side cross-sectional view illustrating a medical device according to a second modification example.
Figure 11:
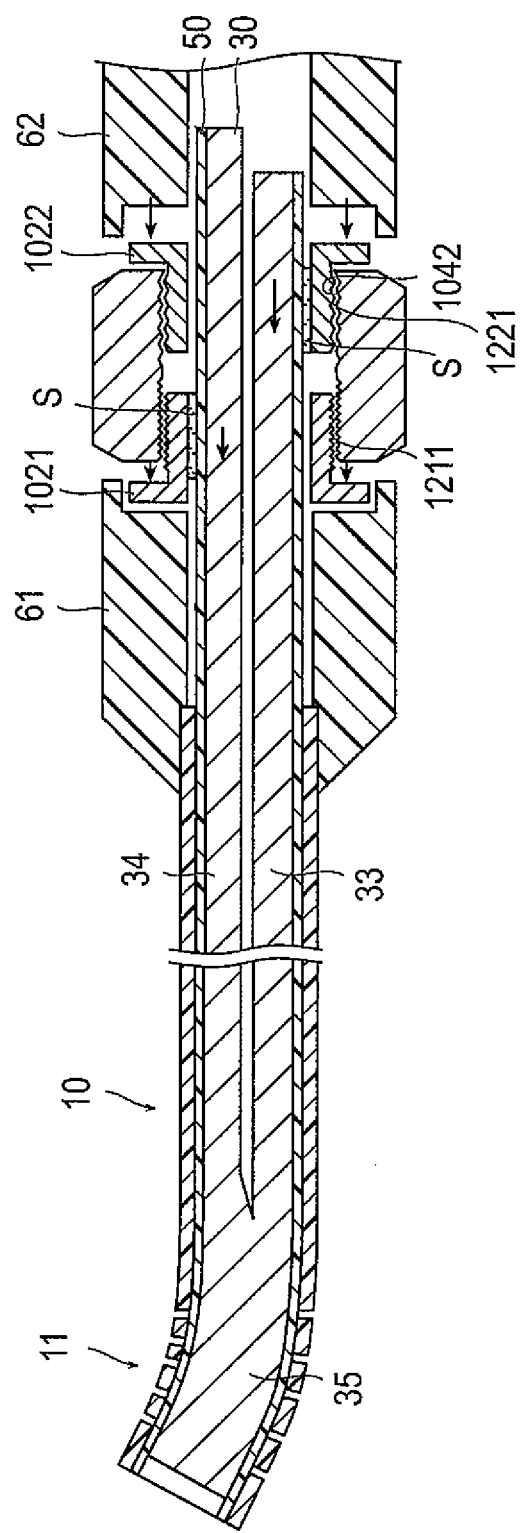
FIG. 11 is a side cross-sectional view illustrating the medical device of FIG. 10 when a distal side of an elongated member is bent upward.

FIG. 10 is a side cross-sectional view illustrating a medical device 4 according to a second modification example. In the above-described second embodiment, as the operation member is rotated so that a meshing amount of the second screw portion 821 formed to have the shorter screw pitch with the second operation screw portion 92 is increased, the operation member causes the elongated member 10 to be bent by moving the first movement member 81 and the second movement member 82 relatively away from each other. However, as illustrated in FIG. 10, a first screw portion 1211 may have a screw pitch which is shorter than that of a second screw portion 1221. As the operation member is rotated so that a meshing amount of the second screw portion 1221 formed to have the longer screw pitch with a second operation screw portion 1042 is increased, the operation member may cause the elongated member 10 to be bent by moving a first movement member 1021 and a second movement member 1022 relatively away from each other. In this case, a position for arranging the adhesive S is upside down as compared to the second embodiment. According to this modification example, as illustrated in FIG. 11, it is possible to suppress bias in the meshing amount between two screw portions located in both ends. Therefore, the load applied to the push-pull member 30 becomes more equal during the bending, thereby improving the operability.

What is claimed is:

1. An actuating member for causing an elongated member for medical use to perform a predetermined operation, the actuating member comprising:
    a first movement member and a second movement member which are located at a proximal side of the elongated member and are configured to be relatively movable toward and away from each other along an axial direction of the elongated member, wherein the first movement member includes a first screw portion, and wherein the second movement member includes a second screw portion;
    a push-pull member comprising:
        a first connection portion connected to the first movement member,
        a first extension portion extending from the first connection portion toward a distal side in the axial direction of the elongated member,
        a second connection portion connected to the second movement member, and
        a second extension portion extending from the second connection portion toward the distal side in the axial direction of the elongated member; and
    an operation member configured to operate the movement of the first movement member and the second movement member, wherein the operation member comprises a tubular member that includes a first operation screw portion configured to mesh with the first screw portion of the first movement member and a second operation screw portion configured to mesh with the second screw portion of the second movement member, the first operation screw portion and the second operation screw portion being formed on an inner peripheral surface of the tubular member, and
    wherein the operation member is configured to operate the movement of the first movement member and the second movement member upon rotation of the operation member,
    wherein the push-pull member is configured to move in the axial direction of the elongated member so as to be pushed and pulled by a movement of the first movement member and the second movement member, and
    wherein the push-pull member is configured to transmit the movement of the first movement member and the second movement member to the elongated member, thereby causing the elongated member to perform at least one of a forward and backward operation and a bending operation.

2. The actuating member according to claim 1, wherein the operation member is configured to respectively move the first movement member and the second movement member in opposite directions to each other along the axial direction, and configured such that the bending operation of the elongated member is performed by moving the first movement member and the second movement member.

3. The actuating member according to claim 2, wherein the second screw portion is threaded in a direction opposite to the first screw portion.

4. The actuating member according to claim 3, wherein the actuating member is configured such that, as the operation member is rotated so that a meshing amount of the first operation screw portion with the first screw portion and a meshing amount of the second operation screw portion with the second screw portion are increased, the operation member causes the elongated member to be bent by moving the first movement member and the second movement member relatively toward each other.

5. The actuating member according to claim 1, wherein the operation member is configured to move the first movement member and the second movement member in the same direction along the axial direction so as to have respectively different movement amounts, and is configured such that the forward and backward operation and the bending operation of the elongated member are performed by moving the first movement member and the second movement member.

6. The actuating member according to claim 5, wherein the second screw portion has a screw pitch different from that of the first screw portion.

7. The actuating member according to claim 6, wherein the actuating member is configured such that, as the operation member is rotated so that a meshing amount of a screw portion formed to have a small screw pitch, out of the first screw portion and the second screw portion, with the first operation screw portion or the second operation screw portion is increased, the operation member causes the elongated member to be bent by moving the first movement member and the second movement member relatively away from each other.

8. The actuating member according to claim 6, wherein the actuating member is configured such that, as the operation member is rotated so that a meshing amount of a screw portion formed to have a large screw pitch, out of the first screw portion and the second screw portion, with the first operation screw portion or the second operation screw portion is increased, the operation member causes the elongated member to be bent by moving the first movement member and the second movement member relatively away from each other.

9. The actuating member according to claim 1, further comprising a sealing portion disposed on an outer periphery of the push-pull member configured to seal a fluid flowing in the push-pull member.

10. The actuating member according to claim 9, further comprising a base portion disposed on an outer periphery of the proximal side of the sealing portion configured to support the first movement member, the second movement member and the push-pull member.

11. A medical device comprising:
    an elongated flexible member; and
    an actuating member for causing the elongated member to perform a predetermined operation, the actuating member comprising:
        a first movement member and a second movement member which are located at a proximal side of the elongated member and are configured to be relatively movable toward and away from each other along an axial direction of the elongated member, wherein the first movement member includes a first screw portion, and wherein the second movement member includes a second screw portion;
        a push-pull member comprising:
            a first connection portion connected to the first movement member,
            a first extension portion extending from the first connection portion toward a distal side in the axial direction of the elongated member, a second connection portion connected to the second movement member, and
a second extension portion extending from the second connection portion toward the distal side in the axial direction of the elongated member; and
an operation member configured to operate the movement of the first movement member and the second movement member, wherein the operation member comprises a tubular member that includes a first operation screw portion configured to mesh with the first screw portion of the first movement member and a second operation screw portion configured to mesh with the second screw portion of the second movement member, the first operation screw portion and the second operation screw portion being formed on an inner peripheral surface of the tubular member,
wherein the push-pull member is configured to move in the axial direction of the elongated member so as to be pushed and pulled by a movement of the first movement member and the second movement member, and
wherein the push-pull member is configured to transmit the movement of the first movement member and the second movement member to the elongated member, thereby causing the elongated member to perform at least one of a forward and backward operation and a bending operation.

12. The medical device according to claim 11, wherein the operation member is configured to respectively move the first movement member and the second movement member in opposite directions to each other along the axial direction, and configured such that the bending operation of the elongated member is performed by moving the first movement member and the second movement member.

13. The medical device according to claim 11, wherein the second screw portion is threaded in a direction opposite to the first screw portion.

14. The medical device according to claim 13, wherein the actuating member is configured such that, as the operation member is rotated so that a meshing amount of the first operation screw portion with the first screw portion and a meshing amount of the second operation screw portion with the second screw portion are increased, the operation member causes the elongated member to be bent by moving the first movement member and the second movement member relatively toward each other.

15. The medical device according to claim 11, wherein the operation member is configured to move the first movement member and the second movement member in the same direction along the axial direction so as to have respectively different movement amounts, and is configured such that the forward and backward operation and the bending operation of the elongated member are performed by moving the first movement member and the second movement member.

16. The medical device according to claim 15, wherein the second screw portion has a screw pitch different from that of the first screw portion.

17. An actuating member for causing an elongated member for medical use to perform a predetermined operation, the actuating member comprising:
a first movement member and a second movement member which are located at a proximal side of the elongated member and are configured to be relatively movable toward and away from each other along an axial direction of the elongated member;
a push-pull member comprising:
a first connection portion connected to the first movement member,
a first extension portion extending from the first connection portion toward a distal side in the axial direction of the elongated member,
a second connection portion connected to the second movement member, and
a second extension portion extending from the second connection portion toward the distal side in the axial direction of the elongated member;
a sealing portion disposed on an outer periphery of the push-pull member and configured to seal a fluid flowing in the push-pull member; and
an operation member configured to operate the movement of the first movement member and the second movement member,
wherein the push-pull member is configured to move in the axial direction of the elongated member so as to be pushed and pulled by a movement of the first movement member and the second movement member, and
wherein the push-pull member is configured to transmit the movement of the first movement member and the second movement member to the elongated member, thereby causing the elongated member to perform at least one of a forward and backward operation and a bending operation.

18. The actuating member according to claim 17, further comprising a base portion disposed on an outer periphery of the proximal side of the sealing portion configured to support the first movement member, the second movement member and the push-pull member.

19. A medical device comprising:
an elongated flexible member; and
an actuating member for causing the elongated member to perform a predetermined operation, the actuating member comprising:
a first movement member and a second movement member which are located at a proximal side of the elongated member and are configured to be relatively movable toward and away from each other along an axial direction of the elongated member;
a push-pull member comprising:
a first connection portion connected to the first movement member,
a first extension portion extending from the first connection portion toward a distal side in the axial direction of the elongated member,
a second connection portion connected to the second movement member, and
a second extension portion extending from the second connection portion toward the distal side in the axial direction of the elongated member;
a sealing portion disposed on an outer periphery of the push-pull member and configured to seal a fluid flowing in the push-pull member; and
an operation member configured to operate the movement of the first movement member and the second movement member,
wherein the push-pull member is configured to move in the axial direction of the elongated member so as to be pushed and pulled by a movement of the first movement member and the second movement member, and
wherein the push-pull member is configured to transmit the movement of the first movement member and the second movement member to the elongated member, thereby causing the elongated member to perform at least one of a forward and backward operation and a bending operation.

20. The medical device according to claim 19, wherein the actuating member further comprises a base portion disposed on an outer periphery of the proximal side of the sealing portion configured to support the first movement member, the second movement member and the push-pull member.

\* \* \* \* \*